(12) United States Patent
Vanegas et al.

(10) Patent No.: US 7,916,949 B2
(45) Date of Patent: Mar. 29, 2011

(54) METHOD OF INSPECTING GRANULAR MATERIAL AND INSPECTION DEVICE FOR CONDUCTING THAT METHOD

(75) Inventors: Oscar Vanegas, Osaka (JP); Mitsuru Shirasawa, Osaka (JP)

(73) Assignee: Panasonic Electric Works, Osaka (JP)

( * ) Notice: Subject to any disclaimer, the term of this patent is extended or adjusted under 35 U.S.C. 154(b) by 893 days.

(21) Appl. No.: 11/816,536

(22) PCT Filed: Feb. 20, 2006

(86) PCT No.: PCT/JP2006/302973
§ 371 (c)(1),
(2), (4) Date: Aug. 17, 2007

(87) PCT Pub. No.: WO2006/090671
PCT Pub. Date: Aug. 31, 2006

(65) Prior Publication Data
US 2009/0123056 A1    May 14, 2009

(30) Foreign Application Priority Data

Feb. 23, 2005 (JP) .................................. 2005-048032
Feb. 23, 2005 (JP) .................................. 2005-048033

(51) Int. Cl.
*G06K 9/48* (2006.01)
(52) U.S. Cl. ....................................... 382/199; 382/192
(58) Field of Classification Search ................... 382/199
See application file for complete search history.

(56) References Cited

U.S. PATENT DOCUMENTS

| 3,150,730 | A | * | 9/1964 | Baur | 177/178 |
| 4,093,941 | A | * | 6/1978 | Bryan et al. | 382/197 |
| 5,974,174 | A | * | 10/1999 | Hozumi | 382/199 |
| 5,978,520 | A | * | 11/1999 | Maruyama et al. | 382/294 |
| 6,124,950 | A | * | 9/2000 | Honda | 358/474 |
| 6,307,964 | B1 | * | 10/2001 | Lin et al. | 382/203 |
| 6,378,572 | B1 | * | 4/2002 | Neubauer et al. | 141/94 |

(Continued)

FOREIGN PATENT DOCUMENTS

JP    4-17665    1/1992

(Continued)

OTHER PUBLICATIONS

Paul L. Rosin, "Shape Partitioning by Convexity," IEEE Transactions on Systems, Man and Cybernetics. Part A: Systems and Humans, vol. 30, No. 2 (2000), XP011056303, ISSN: 1083-4427, Mar. 1, 2000.

(Continued)

*Primary Examiner* — Sath V Perungavoor
(74) *Attorney, Agent, or Firm* — Greenblum & Bernstein, P.L.C.

(57) ABSTRACT

A method of inspecting granular material and an inspection device for conducting that method, wherein agents (10*a*, 10*b*) to be inspected are imaged, the pixel value of each pixel of images thus picked up is digitized, a plurality of reference points are dispersed along the outlines of massive regions corresponding to the agents (10*a*, 10*b*) in digital images, the numbers of other reference points that can be viewed through massive regions from individual reference points are counted, a reference point giving a minimum counted value is extracted as a base point, and the number of these base points is counted as the number of granular materials. Accordingly, the number of granular materials can be counted accurately even if a plurality of granular materials to be inspected overlap each other, are in contact with each other, or any agent having a groove in one surface is erected.

15 Claims, 13 Drawing Sheets

U.S. PATENT DOCUMENTS

| | | |
|---|---|---|
| 7,151,853 B2 * 12/2006 | Roh et al. | 382/195 |
| 2002/0145616 A1 * 10/2002 | Doan | 345/629 |
| 2009/0123056 A1 * 5/2009 | Vanegas et al. | 382/141 |

FOREIGN PATENT DOCUMENTS

| | | |
|---|---|---|
| JP | 7-200770 | 8/1995 |
| JP | 9-231342 | 9/1997 |
| JP | 2004-234132 | 8/2004 |

OTHER PUBLICATIONS

European Search Report that issued with respect to patent family member European Patent Application No. 06714113.5, mailed Apr. 28, 2010.

English Language Abstract of JP 2004-234132, Nov. 20, 2007.

English Language Abstract of JP 9-231342, Nov. 20, 2007.

English Language Abstract of JP 04-017665, Nov. 20, 2007.

* cited by examiner (a)

(b)

(a)

(b)

(a)

(b)

(a)

(b)

(a)

(b)

(a)

(b)

METHOD OF INSPECTING GRANULAR MATERIAL AND INSPECTION DEVICE FOR CONDUCTING THAT METHOD

TECHNICAL FIELD

The present invention relates to a method of inspecting granular material such as solid agents and an inspective device for conducting the method.

BACKGROUND ART

Generally, when a plurality of agents are administered to a patient in medical facilities such as hospitals, the agents taken at a time are packed together with a packing material and given to a patient so that the patient may not take wrong types of agents or the wrong number of agents by mistake. In correct dosage or combination of agents can cause serious adverse effects. For this reason, sorting and packing operations of agents are required to be manually made. However, such manual sorting and packing operations can cause errors. Thus, there have been conventionally provided inspective devices for granular materials for inspecting the types and quantity of packed agents (refer to, for example, Japanese Published Examined Application Publication No. 4-17665).

In an inspective device for granular material disclosed in Japanese Published Examined Application Publication No. 4-17665, an image of an agent is picked up by an imaging means such as a CCD camera and the image is subjected to data processing such as binarization to obtain image data. Then, the data is processed to find area, circumference and complexity of each object in the image. Based on the area and the complexity, it is determined whether or not the object in the image is an agent and the number of agents is acquired. Complexity means a value obtained by dividing a square of circumference by area.

DISCLOSURE OF INVENTION

However, if an image of a plurality of packed agents is picked up in a partially overlapped state, the above-mentioned inspective device for granular material causes the problem that the number of agents is incorrectly counted. For example, as shown in FIG. 12(a), if two agents 10a, 10b placed on an inspection table 1 overlap with each other, the inspective device for granular material disclosed in Patent document 1 cannot correctly detect area and circumference of objects in the image as the device determines whether or not the objects are agents based on the area and complexity of the objects. Thus, the device cannot correctly determine the agents. Alternatively, if the agents 10a, 10b have a groove on one surface thereof as shown in FIG. 13 (a) and are erected as shown in FIG. 13(b), a dent occurs in a part of outlines of the agents. Accordingly, the device cannot correctly the circumferences of the agents and thus, cannot correctly count the number of agents.

To solve the above-mentioned problems, a method of imaging the agents from above as well as a plurality of directions is considered. However, this method requires a plurality of imaging means or a mechanism for moving an imaging means to a plurality of imaging positions, disadvantageously resulting in an increase in costs.

A method of picking up an image of the agents and processing the image after overlap or contact of the agents is eliminated by vibrating the inspection table is also considered. However, this method requires a mechanism for vibrating the inspection table, disadvantageously causing an increase in costs.

In consideration of these problems, an object of the present invention is to provide a method of inspecting granular material and an inspective device for conducting the method which can count accurately the number of granular materials to be inspected even if the granular materials overlap each other, are contact with each other, or any agent having a groove in one surface is erected.

According to the present invention, a method of inspecting granular material in a digital image obtained by picking up an image of an imaging region including granular materials to be inspected and digitarizing a pixel value of each pixel of the picked up image, in the case where one massive region is formed of a plurality of material regions corresponding the granular materials which are in contact with each other, for inspecting the granular materials existing in the image region by separating the individual material regions from the massive region comprises:

first extraction processing of extracting the massive region as a target region of image processing from the digital image;

setting processing of dispersely setting a plurality of reference points along the outline of the target region on an inner side of the target region extracted by the first extraction processing;

counting processing of counting the number of other reference points which can be viewed through the target region from individual reference points set by the setting processing;

second extraction processing of extracting a reference point giving a minimum count value obtained by the counting processing as a base point from the plurality of reference points in the target region;

third extraction processing of selecting all reference points which can be viewed through the target region from the base point extracted by the second extraction processing and extracting a region formed by connecting the selected reference points to the base point as the material region of the granular material; and fourth extraction processing of extracting a region in the target region extracting by the third extraction processing except for the material region as a new target region, and by repeatedly performing the second to fourth extraction processing, the number of the extracted base points can be counted as the number of granular materials.

Thus, in the digital image, the material regions corresponding to the granular materials can be separated one by one, and even if a plurality of granular material are in contact with each other or overlap each other, the number of granular materials can be correctly counted on the basis of the number of the extracted base points.

According to the present invention, the image processing section may perform fifth extraction processing of extracting all reference points which can view only one base point of the plurality of base points extracted by repeatedly performing the second to fourth extraction processing through the target region extracted by the first extraction processing as base point assigned reference points for the base point, forms connection segments connecting the base point extracted by performing the second to fourth extraction processing to all base point assigned reference points assigned to the base point which are extracted by the fifth extraction processing, and defines a region surrounded by all connection segments thus formed as a material region of the granular material corresponding to the base point. Whereby, a region closer to an actual region of the granular material can be extracted as the material region.

The connection segment may be formed by connecting two points of all base point assigned reference points assigned to each base point which are extracted by the fifth extraction processing among the plurality of base points extracted by repeatedly performing the second to fourth extraction processing to each other. Whereby, a region closer to an actual region of the granular material can be extracted as the material region.

The connection segment may be formed by performing sixth extraction processing of extracting reference points other than the base point assigned reference points extracted by the fifth extraction processing among all reference points as undistinguished reference points, determining a material region which can be viewed through the target region extracted by the first extraction processing from the undistinguished reference points extracted by the sixth extraction processing as a material region corresponding to the undistinguished reference points, and connecting two points among the base point corresponding to the material region thus determined, base point assigned reference points and undistinguished reference points to each other. Whereby, a region closer to an actual region of the granular material can be extracted as the material region.

According to the present invention, the image processing section may form a plurality of search lines radially extending from the undistinguished reference points extracted by the sixth extraction processing at substantially regular angles are formed, and add a region defined by the individual search lines thus formed and the connection segment connecting two points of all base point assigned reference points assigned to the base point extracted by the fifth extraction processing to each other which intersect the search lines to the material region corresponding to the intersecting connection segment. Thus, the material region to which the undistinguished reference points are assigned can be determined as the material region which is the closest to the undistinguished reference point, and the region closer to the region of the actual granular material can be extracted as the material region.

According to the present invention, the image processing section performs seventh extraction processing of extracting reference points which can view only one base point among a plurality of base points extracted by repeatedly performing the second to fourth extraction processing through the target region extracted by the first extraction processing and are disposed on the opposite side to the base point across the center of the target region. When at least part of connection segments connecting shape determination points corresponding to one base point extracted by the seventh extraction processing to the shape determination points corresponding to other base point passes outside of the target region, the image processing part may determine that the plurality of base points are assigned to different granular material and count the number of granular materials on the basis of the number of determined base points assigned to different granular materials. Thus, even if the granular material having a groove on one surface is erected, the image processing section can determine that two base points are assigned to the same granular material as the shape determination points are not extracted by the seventh extraction processing, and thus the number of granular materials can be correctly identified without wrongly detecting two granular materials.

According to the image processing method which can determine that two base points are assigned to the same granular material even if the granular material having a groove on one surface is erected and the two base points are extracted as described above, the image processing section performs eighth extraction processing of extracting a region surrounded by a first connection segment connecting one base point to the other base point and the outline as a first region and a region surrounded by a second connection segment connecting the shape determination points corresponding to the two base points extracted by the seventh extraction processing to each other and the outline as a second region. When a difference between an area of the first region and that of the second region extracted by the eighth extraction processing is smaller than a predetermined reference area, the image processing section may determine that the two base points are assigned to different granular material, and count the number of granular materials on the basis of the number of determined base points assigned to different granular materials.

A difference between a maximum distance from a point on the outline forming the first region extracted by the eighth extraction processing to the first connection segment and a maximum distance from a point on the outline forming the second region extracted by the eighth extraction processing to the second connection segment is obtained. When the difference in distance is shorter than a predetermined reference distance, it may be determined that the two base points are assigned to different granular materials. Whereby, compared to the case of directly obtaining the areas of the first region and the second region, time required for calculation processing can be reduced.

When a plurality of shape determination points are extracted by the seventh extraction processing with respect to the base point extracted by repeatedly performing the second to fourth extraction processing, the shape determination point having the longest distance from the corresponding base point may be selected from the plurality of shape determination points, and using the selected shape determination point, the second connection segment may be formed. Whereby, calculation time required for determination processing can be reduced.

According to the present invention, in an inspective device for granular material comprising: an imaging means for picking up an image of an imaging region including granular materials to be inspected; and an image processing section, in the case where one massive region is formed of a plurality of material regions corresponding to the granular materials which are in contact with each other in a digital image obtained by digitarizing a pixel value of each pixel of the image picked up by the imaging means, for separating the individual material regions from the massive region, the image processing section includes a first extraction means for extracting the massive region from the digital image, a setting means for dispersely setting a plurality of reference points along the outline of the target region on the inner side of the target region extracted by the first extraction means, a counting means for counting the number of other reference points which can be viewed through the target region from the individual set reference points, a second extraction means for extracting a reference point giving a minimum count value counted by the counting means as a base point from the plurality of reference points existing in the target region, a third means for selecting all reference points which can be viewed through the target region from the base point extracted by the second extraction means and extracting a region formed by connecting the selected reference points to the base point as a material region of the granular material, a fourth means for extracting a region other than the material region of the target region extracted by the third extraction means as a new target region, a seventh extraction means for extracting reference points which can view only one base point of a plurality of base points extracted by repeatedly operating the second to fourth extraction means and are located on the opposite side to the base point across the center of the target region as shape determination points, and a means for determining that the plurality of base points are assigned to different granular materials when at least part of connection segments connecting shape determination points corresponding to one base point extracted by the seventh extraction processing to the shape determination points corresponding to other base point passes outside of the target region and counting the number of granular materials on the basis of the number of base points assigned to the determined different granular materials. Thus, even if a plurality of granular materials are in contact with each other or overlap each other, the number of granular materials can be correctly counted on the basis of the number of extracted base points.

BEST MODE FOR CARRYING OUT THE INVENTION

First Embodiment

Figure 1:
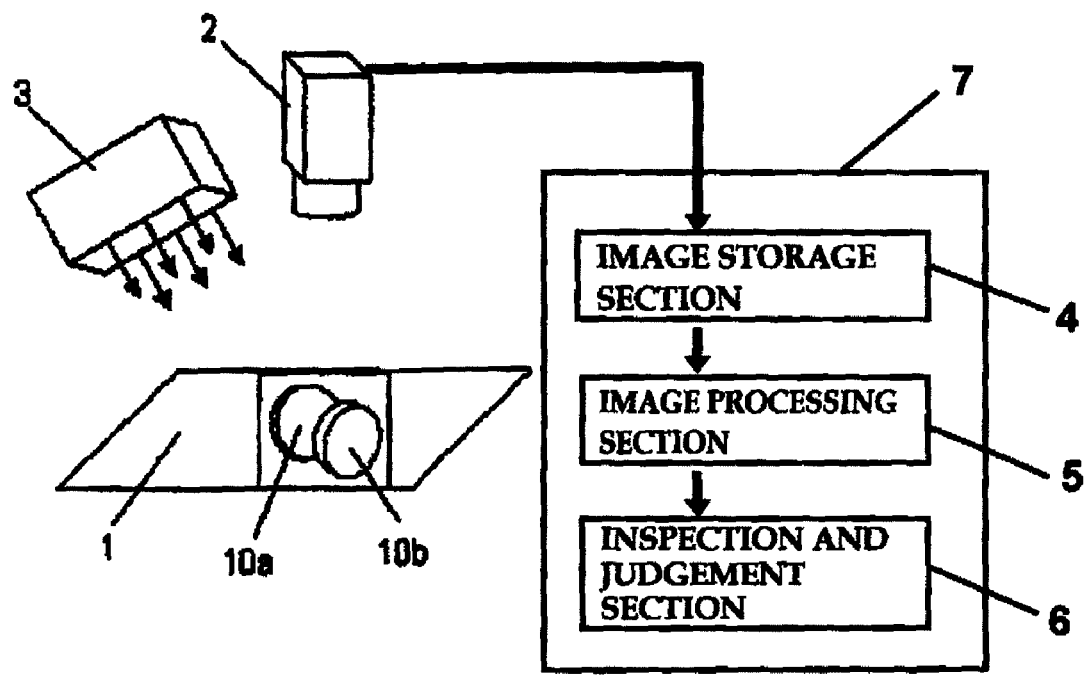
FIG. 1 is a schematic configuration view of an inspection device for granular material in accordance with First embodiment of the present invention.

Hereinafter, a method of inspecting granular material and an inspective device for conducting the method in accordance with First embodiment will be described. FIG. 1 shows schematic configuration of the inspective device for granular material in accordance with this embodiment. The inspective device for granular material has an inspection table 1 for mounting granular materials to be inspected (agents 10a, 10b) thereon, an imaging means 2 (for example, CCD camera) installed above the inspection table 1 for picking up an image of the agents 10a, 10b, a lighting equipment 3 disposed on the same side as the imaging means 2 with respect to the inspection table 1 for applying light to the granular materials mounted on the inspection table 1, an image storage section 4 for storing binarized image obtained by binarizing shading information of an image signal picked up by the imaging means 2 using an appropriate threshold, an image processing section 5 for processing the binarized image stored in the image storage section 4 and dividing the image into material regions corresponding to the granular materials and an inspection and judgment section 6 for counting the number of granular materials on the basis of the number of material regions into which the image is divided by the image processing section 5. The image storage section 4, the image processing section 5 and the inspection and judgment section 6 form an image processing/inspection and judgment section 7.

Due to the light applied by the lighting equipment 3, a difference between a background part and parts corresponding to the agents 10a, 10b in luminance becomes large. Further, the surface of the inspection table 1 has a low optical reflectance. Thus, when the lighting equipment 3 applies light to the inspection table 1, in the image picked up by the imaging means 2, the parts of the agents 10a, 10b look lighter and the background part (the surface of the inspection table 1) look darker. In this manner, a relatively large luminance difference occurs between the outlines of the agents 10a, 10b and the background. By binarizing a signal value concerning shading information of the image signal output from the imaging means 2, the outlines of the agents 10a, 10b can be easily separated from the background. Alternatively, the image signal obtained by the imaging means 2 may be multiple-valued by A/D conversion without being binarized and the image data of the gray-scaled image may be stored in the image storage section 4. When the gray-scaled image is used, differential processing can be applied, and thus judgment accuracy can be improved.

The binarized image obtained by binarizing the image signal picked up by the imaging means 2 is a digital image having pixels of pixel values 0 or 1 and is stored in the image storage section 4 formed of a RAM. The image storage section 4 is used as a storage region of the binarized image as well as a storage region for operations of various image processing described later. The binarized image stored in the image storage section 4 is input to the image processing section 5 and subject to the following image processing. The image processing section 5 recognizes shape of the agents 10a, 10b, and based on the recognition result, the inspection and judgment section 6 identifies the number of agents 10a, 10b. A monitor (not shown) such as a CRT and a liquid crystal display is connected to the image processing section 5. The image picked up by the imaging means 2, the image binarized by a binarization processing section (not shown), result recognized by the image processing section 5 and so on are displayed on the monitor.

According to the method of inspecting granular material of this embodiment, for example, a plurality of agents 10a, 10b packed in one packing bag are mounted on the inspection table 1 and determines whether or not the number of the agents 10a, 10b mounted on the inspection table 1 is correct on the basis of the image of agents 10a, 10b picked up by the imaging means 2. After the number is finally determined, the agents 10a, 10b are packed together with the packing material. If the packing material is transparent or semitransparent and the image of the agents 10a, 10b is picked up by the imaging means 2, the outlines of the agents 10a, 10b in the image can be recognized as in the case where the agents are not packed with the packing material, the agents 10a, 10b packed with the packing material in advance may be mounted on the inspection table 1 and imaged.

Figure 2:
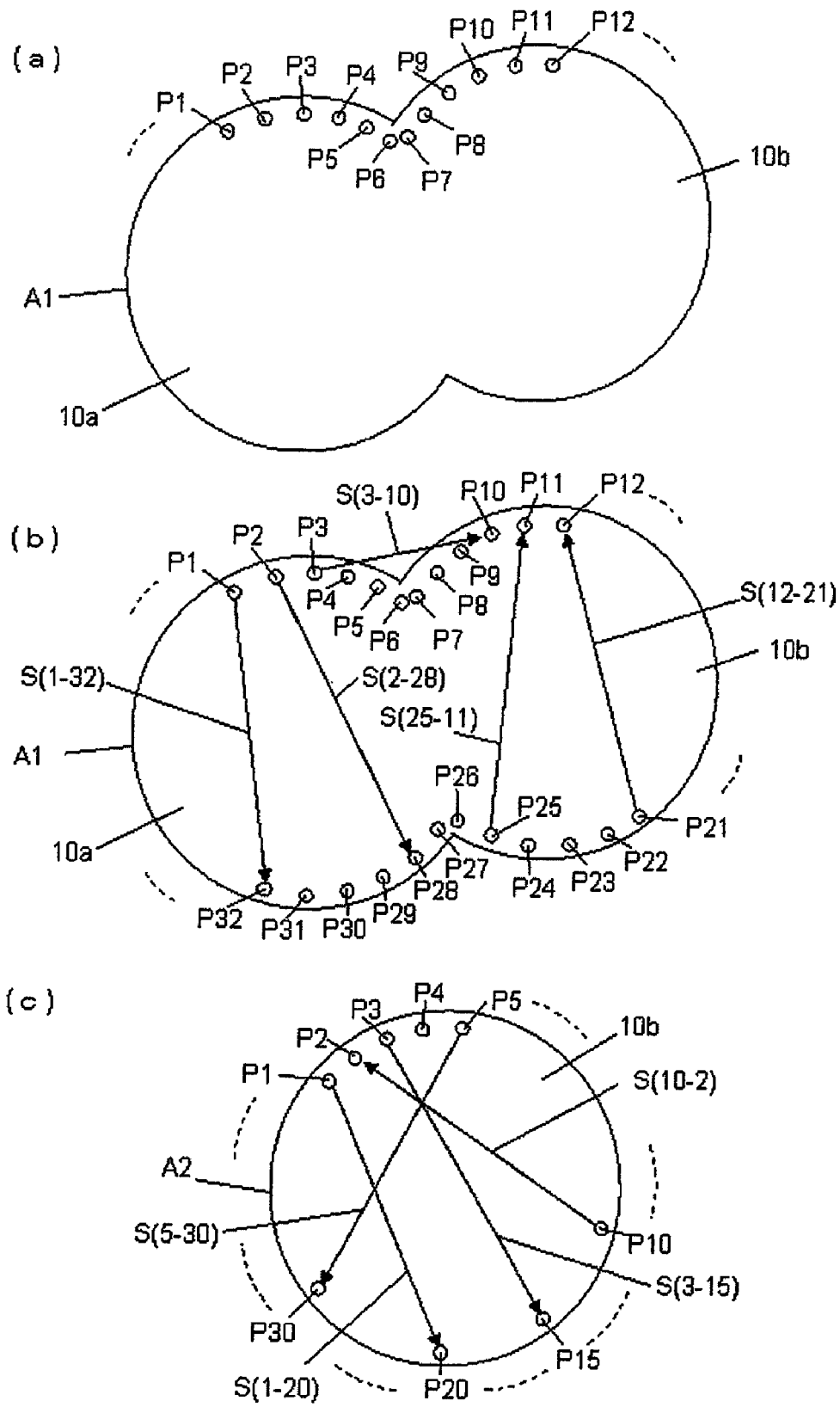
FIGS. 2(a), 2(b) and 2(c) are explanation views of an image processing method.

Next, in the method of inspecting granular material in accordance with this embodiment, a specific example of an image processing method by the image processing section 5 will be described. FIG. 2(a) shows a binarized image stored in the image storage section 4 in the case where two round tablets (agents 10a, 10b) are mounted on the inspection table 1 so as to partially overlap each other. In the binarized image, one continuous region corresponding to the two agents 10a, 10b (hereinafter referred to as a massive region A1) is represented. In such case, to count the number of the agents 10a, 10b, a region corresponding to each of the agents 10a, 10b (hereinafter referred to as a material region) needs to be separated from the massive region A1 in the binarized image.

First, the image processing section 5 performs first extraction processing of extracting the massive region A1 as a target region of image processing from the binarized image stored in the image storage section 4. Then, setting processing of setting an appropriate number of pixels in the vicinity of the outline of the extracted massive region A1 as reference points is performed. The reference points are set so as to be dispersed at substantially regular intervals along outlines of the massive region A1 or inner from the outlines of the massive region A1 by a few pixels.

Here, the case where only one agent 10a is mounted on the inspection table 1 without being contact with or overlap the other agent is used as an example. FIG. 2(c) shows a binarized image stored in the image storage section 4 in the case where an image of one round tablet (agent 10a) is picked up. A region corresponding to the agent 10a (referred to as a massive region A2) is represented in the binarized image. First, the image processing section 5 sets all reference points dispersed along the outline of the massive region A2 (for example, P1, P2, P3, P4, P5 . . . ) and prepares connection segments interconnecting between the reference points (P1 . . . ) (for example, S(1-20), S(2-10), S(3-15), S(5-30) . . . ). The image processing section 5 performs counting processing of counting the number of connection segments, pixels on which have the same pixel value (0 or 1). Thus, the number of other reference points which can be viewed through the massive region A2 from individual reference points is counted.

Here, arbitrary reference points set in the massive region A2 are defined as a reference point Pm and a reference point Pn, and a segment connecting the reference point Pn to the reference point Pm is defined as a connection segment S(m-n). When the connection segment S(m-n) passes through the massive region A2, pixels on the connection segment S(m-n) have the same value (0 or 1). Thus, by comparing the pixel value of each pixel on the segment with each other, it is determined whether or not the connection segment S(m-n) passes through only the massive region A2. In the case of a multi-valued image, if the pixel value of the pixels on the connection segment is a density value in a predetermined range, it is determined that the connection segment passes through only the massive region A2. In the example shown in FIG. 2(c), it is determined that all of the connection segments S(1-20), S(2-H)), S(3-15), S(5-30) . . . pass through only the massive region A2. The number of the other reference points which can be viewed through the massive region A2 from all reference points is the same value (given that the total number of the reference points P1 . . . is k, (k−1)).

Even if two partially overlapped agents 10a, 10b forms the massive region A1 as shown in FIG. 2(b), the image processing section 5 locates a plurality of reference points along the outline of the massive region A1 at substantially regular intervals. Next, the image processing section 5 prepares connection segments (for example, S(1-32), S(2-28), S(3-10), S(11-25), S(12-21) . . . ) connecting the individual reference points (for example, P1, P2, P3, P11, P12 . . . ) to other reference points (for example, P32, P28, P10, P25, P21 . . . ). In this case, some connection segments (for example, segment S(3-10)) pass the outside of the massive region A1. That is, when the image processing section 5 counts the number of the other reference points which can be viewed through the massive region A1 from the plurality of reference points in the massive region A1 (hereinafter referred to a count value), some reference points cannot be viewed through the massive region A1 from reference points in the vicinity of an overlapped portion of the agents 10a, 10b (for example, reference point P5, P6, P25, P30, etc.), which are located behind dented parts of the outline. For this reason, the count value of the reference points in the vicinity of an overlapped portion of the agents 10a, 10b is less than that of the reference point in other portion.

Therefore, the image processing section 5 performs the counting processing of obtaining the count values of individual reference points in the target region (massive region A1) and stores the count values obtained by the counting processing in the image storage section 4. The following Table 1 shows an example of the count values of the individual reference points dispersely located as shown in FIG. 2(b).

[Table 1]
Reference Point
Count Value

Following the above-mentioned counting processing, the image processing section 5 performs second extraction processing of extracting a reference point giving a minimum count value obtained by the counting processing (refer to Table 1) as a base point from the plurality of reference points in the massive region A1. In the example shown in FIG. 2(b), since the count value of the reference point P3 is the smallest as apparent from Table 1, the image processing section 5 extracts the reference point P3 as the base point. As a result of the counting processing, a plurality of reference points of the same granular material or different granular materials may have a minimum count value. In this case, the image processing section 5 arbitrarily selects one reference point as a base point from the reference points giving the minimum count value and performs below-described processing with respect to the extracted base point. Even if the number of granular materials is counted using any reference point as the base point, the same result is obtained. On the contrary, as a result of the counting processing, if the count values at all reference points are the same, for example, as shown in FIG. 2(c), the image processing section 5 determines that the massive region A2 corresponds to one granular material, finishes subsequent processing and determines that the number of granular material corresponding to the massive region A2 is one.

Figure 3:
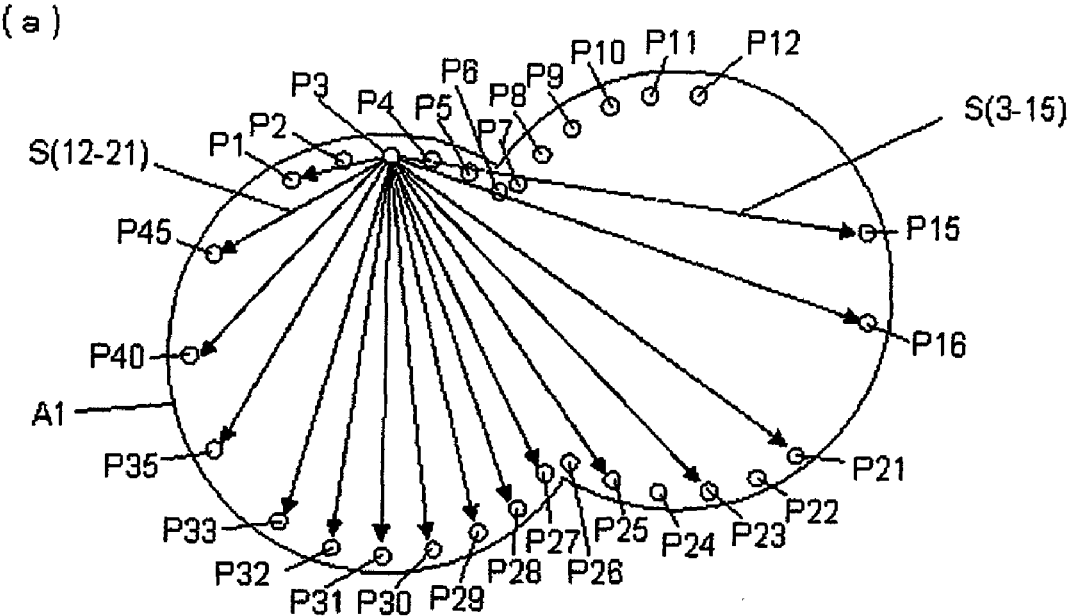
FIGS. 3(a) and 3(b) are explanation views of the image processing method.
Figure 3:
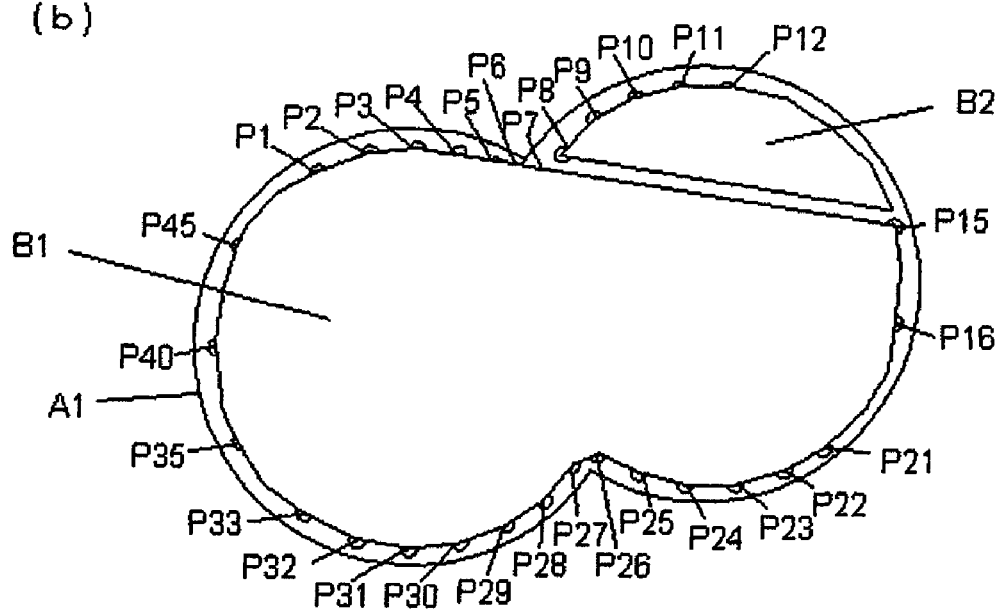

Next, when the base point P3 is extracted by the second extraction processing, as shown in FIG. 3(a), the image processing section 5 selects all reference points which can be viewed through the massive region A1 from the base point P3 (for example, P1, P2, P4 to P7, P15 to P45) and forms connection segments connecting the base point P3 to the selected reference points. Then, the image processing section 5 performs third extraction processing of extracting a region surrounded by these connection segments as a material region B1 corresponding to one granular material (refer to FIG. 3(b)).

Subsequently, the image processing section 5 performs fourth extraction processing of extracting a region in the massive region A1 other than the material region B1 as a new target region A3 (not shown), selecting a reference point giving a minimum count value obtained by the counting processing (refer to Table 1) (here, a reference point P10) from a plurality of reference points in the target region A3 (for example, P8, P9 . . . ) and extracting the reference point P10 as a new base point. When the new base point P10 is extracted, the image processing section 5 selects all reference points which can be viewed through the target region A1 from the base point P10 (for example, P8, P9, P10 . . . ) and forms connection segments connecting the selected reference points to the base point P10. Then, a region surrounded by the connection segments is extracted as a material region B2 corresponding to one material (refer to FIG. 3(b)). At this time, a region formed of the material regions B1, B2 becomes almost equal to the massive region A1. No reference point exists in the region in the massive region A1 except for the material regions B1, B2. The image processing section 5 finishes extraction processing of the base points. The inspection and judgment section 6 determines the number of extracted base points (2 in this embodiment) as the number of granular materials in the massive region A1.

As described above, the image processing section 5 repeatedly processing of extracting a reference point giving a minimum count value as a base point from reference points in the target region (second extraction processing), extracting a region formed by connecting reference points which can be viewed through the target region from the base point to the base point as a material region (third extraction processing) and extracting a region in the target region other than the material region as a new target region (fourth extraction processing). Whereby, the material regions B1, B2 can be separated one by one from the massive region A1. Even if a plurality of granular materials overlaps each other, the number of granular materials can be correctly counted on the basis of the number of the extracted base points.

Second Embodiment

A method of inspecting granular material and an inspective device for conducting the method in accordance with Second embodiment of the present invention will be described. The inspection device has the same configuration as the inspection device in First embodiment. The same reference numerals are given to elements common to First embodiment and description thereof is omitted (the same applies to the following embodiments).

In First embodiment, after the base point is extracted, a region surrounded by the connection segments connecting the reference points which can be viewed from the base point to the base point is extracted as a material region. Thus, the material region B1 shown in FIG. 3(b) includes a region corresponding to the agent 10a as well as a region corresponding to the agent 10b. That is, according to the image processing method described in First embodiment, regions which are very different from actual material regions of the agents 10a, 10b are extracted. In this embodiment, however, material regions close to the actual regions of the agents 10a, 10b can be extracted by below-described image processing of the image processing section 5. Thus, the number of granular materials can be counted more correctly.

Figure 4:
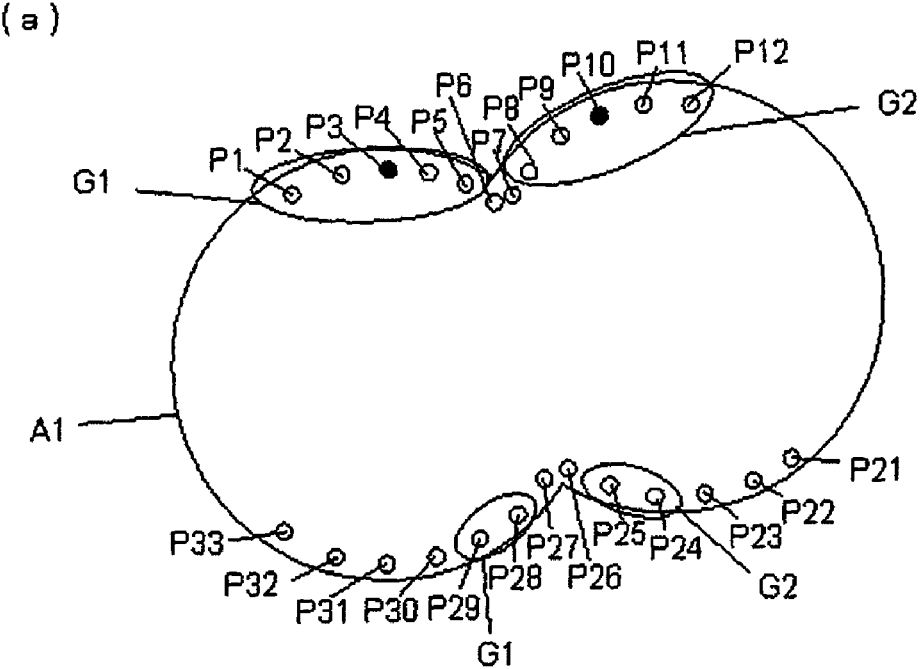
FIGS. 4(a) and 4(b) are explanation views of an image processing method by an inspective device for granular material in accordance with Second embodiment of the present invention.
Figure 4:
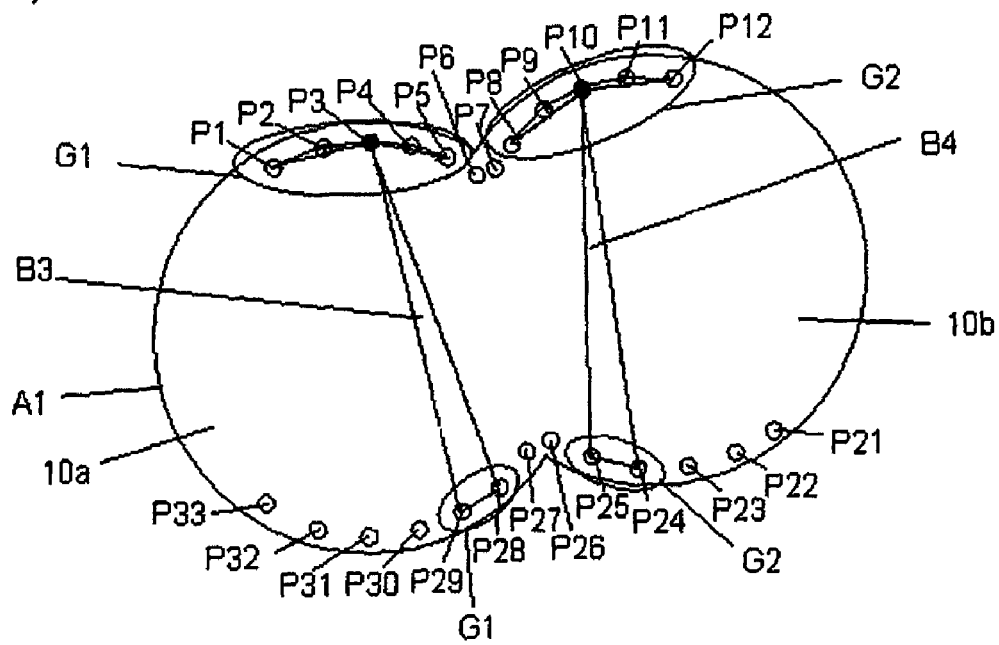

In this embodiment, first, in the case where two agents 10a, 10b overlap each other as shown in FIG. 4 (a), the image processing section 5 extracts two base points P3, P10 by performing the second to fourth extraction processing described in First embodiment. Then, the image processing section 5 performs fifth extraction processing of extracting all reference points which can view only one base point (P3 or P10) through the region and defining all of the extracted reference points as base point assigned reference points. Specifically, the image processing section 5 forms two connection segments connecting all reference points in the massive region A1 to the base points P3, P10, respectively. When pixel values of pixels on only one of the two connection segments are the same value, the image processing section 5 determines that the reference point forming the connection segments can view only one base point. Here, when the two agents 10a, 10b overlap each other as shown in FIG. 4(a), the reference point which can view only one of the base points P3, P10 corresponding to the agents 10a, 10b exist on the periphery of the overlap portion of the agents 10a, 10b (hidden portion of the massive region A1). For example, in FIG. 4(a), the image processing section 5 extracts reference points P1, P2, P4, P5, P28, P29 for the base point P3 as base point assigned reference points G1 and reference points P8, P9, P11, P12, P24, P25 for the base point P10 as base point assigned reference points G2.

Following the extraction processing of the base point assigned reference points G1, G2 assigned to the base points P3, P10, as shown in FIG. 4(b), the image processing section 5 forms connection segments connecting the base point P3 to the base point assigned reference points G1 (for example, S(3-1), S(3-2), S(3-4), S(3-5), S(3-28), S(3-29)) and extracts the connection segments as a material region B3 of the agent 10a corresponding to the base point P3. Similarly, the image processing section 5 forms connection segments S(10-8), S(10-9), S(10-11), S(10-12), S(10-24), S(10-25) connecting the base point P10 to the base point assigned reference points G2 and extracts the connection segments as a material region B4 of the agent 10b corresponding to the base point P10.

As described above, using the base point assigned reference points G1 which can view only the base point P3 as reference points of the granular material assigned to the base point P3, the image processing section 5 extracts connection segments connecting the base point P3 to the base point assigned reference points G1 as the material region corresponding to the base point P3. In a similar manner, the image processing section 5 extracts the material region corresponding to the base point P10. Whereby, the image processing section 5 can extract a region close to the actual granular materials of the agents 10a, 10b as material regions.

Third Embodiment

Figure 5:
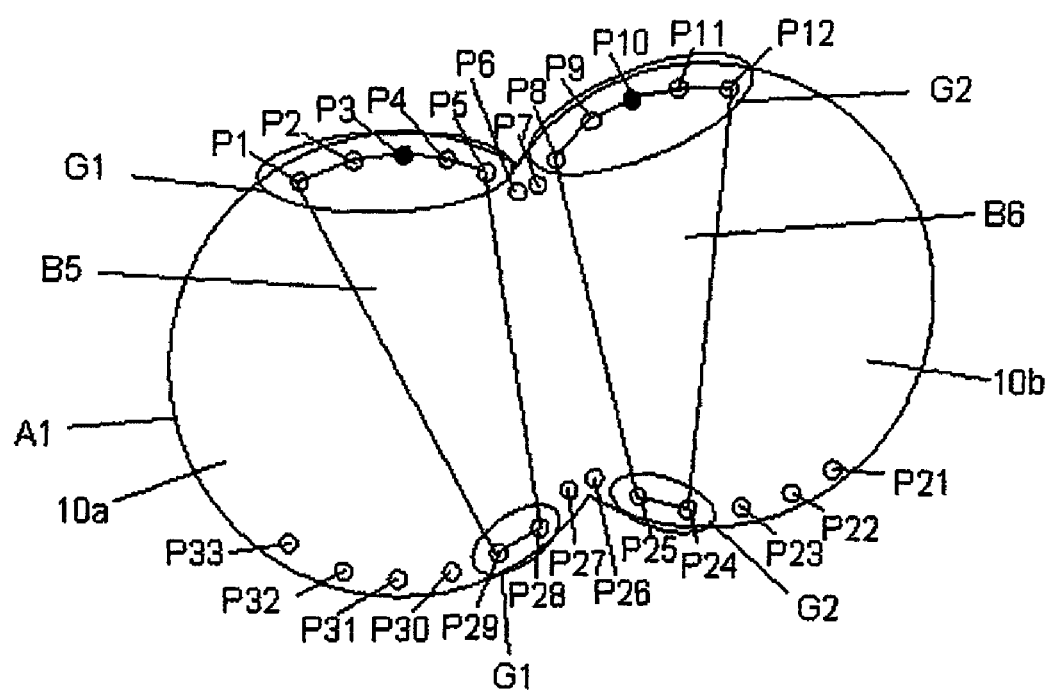
FIG. 5 is an explanation view of an image processing method by an inspective device for granular material in accordance with Third embodiment of the present invention.

A method of inspecting granular material and an inspective device for conducting the method in accordance with Third embodiment of the present invention will be described. In this embodiment, as shown in FIG. 5, in the case where two agents 10a, 10b overlap each other, the image processing section 5 extracts the two base points P3, P10 by repeatedly performing the second to fourth extraction processing described in First embodiment and then, extracts the base point assigned reference points G1, G2 assigned to the base points P3, P10, respectively, by performing the fifth extraction processing described in Second embodiment.

Next, the image processing section 5 forms connection segments connecting the base point P3 to all reference points in the base point assigned reference points G1 and extracts a region surrounded by the connection segments (B5) as a material region of the agent 10a corresponding to the base point P3. The image processing section 5 forms connection segments connecting the base point P10 to all reference points in the base point assigned reference points G2 and extracts a region surrounded by the connection segments (B6) as a material region of the agent 10b corresponding to the base point P10. Thus, compared with Second embodiment, the image processing section 5 can extract regions closer to the actual regions of the agents 10a, 10b as material regions.

Fourth Embodiment

Figure 6:
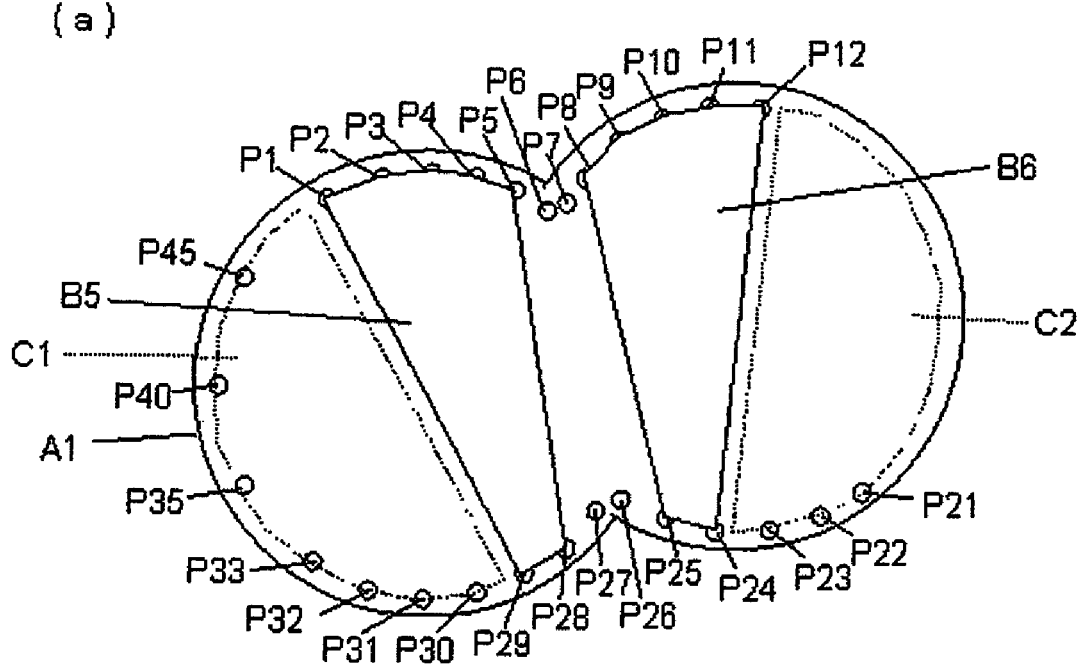
FIGS. 6(a) and 6(b) are explanation views of an image processing method by an inspective device for granular material in accordance with Fourth embodiment of the present invention.
Figure 6:
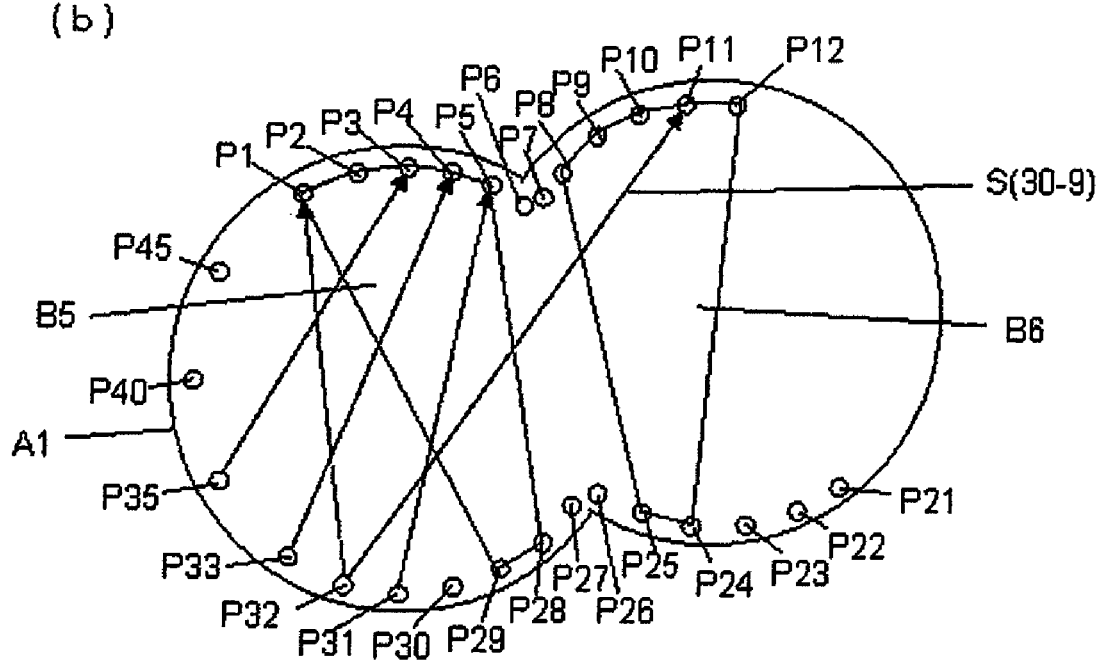

A method of inspecting granular material and an inspective device for conducting the method in accordance with Fourth embodiment of the present invention will be described. According to the image processing methods in Second and Third embodiments, the portion where the agents 10a, 10b are contact with each other or overlap each other is extracted as the material region. However, unoverlapped portion is not extracted. For example, according to the image processing method in Third embodiment, as shown in FIG. 6 (a), the material regions B5, B6 are extracted from only the overlapped portions in the regions corresponding to the agents 10a, 10b and regions C1, C2 are not extracted as material regions.

In this embodiment, after extracting the material regions B5, B6 according to the method described in Third embodiment, the image processing section 5 performs sixth extraction processing of extracting reference points in two regions other than the material regions B5, B6 (referred to as undetermined regions C1, C2) as undistinguished reference points. The following processing is applied to the reference points in the material regions B5, B6 from each reference point of the undistinguished reference points extracted by the sixth extraction processing. For example, as shown in FIG. 6(b), using the undistinguished reference points (for example, P30, P31, P32, P33, P34 . . . ) in the undetermined region C1 as starting points, the image processing section 5 forms connection segments connecting the undistinguished reference points to the reference points in the material regions B5, B6 (for example, P1 . . . ) and detects which of the material regions is initially passed by the connection segments each having the undistinguished reference point as the starting point. The image processing section 5 determines the material region which is passed by the connection segment having each undistinguished reference point as the starting point as a material region assigned to the undistinguished reference point. For example, when two connection segments (for example, S(30-1), S(30-9) . . . ) connecting reference points P1, Pn in material regions B5, B6 are formed using a reference point P30 in the undetermined region C1 as the starting point, both of the connection segments pass the material region B5 first. Thus, the image processing section 5 determines the reference point P30 as the reference point in the material region of the agent 10a.

By applying the above-mentioned processing to all undistinguished reference points in the undetermined regions C1, C2, the image processing section 5 determines which material region of the granular material is assigned to each of all undistinguished reference points. By including a region surrounded by the connection segments connecting the individual undistinguished reference points to the reference points in the material region which is initially passed by the undistinguished reference points in the material region B5 or B6, the material regions B5, B6 can be get closer to the actual regions corresponding to the agents 10a, 10b.

Figure 7:
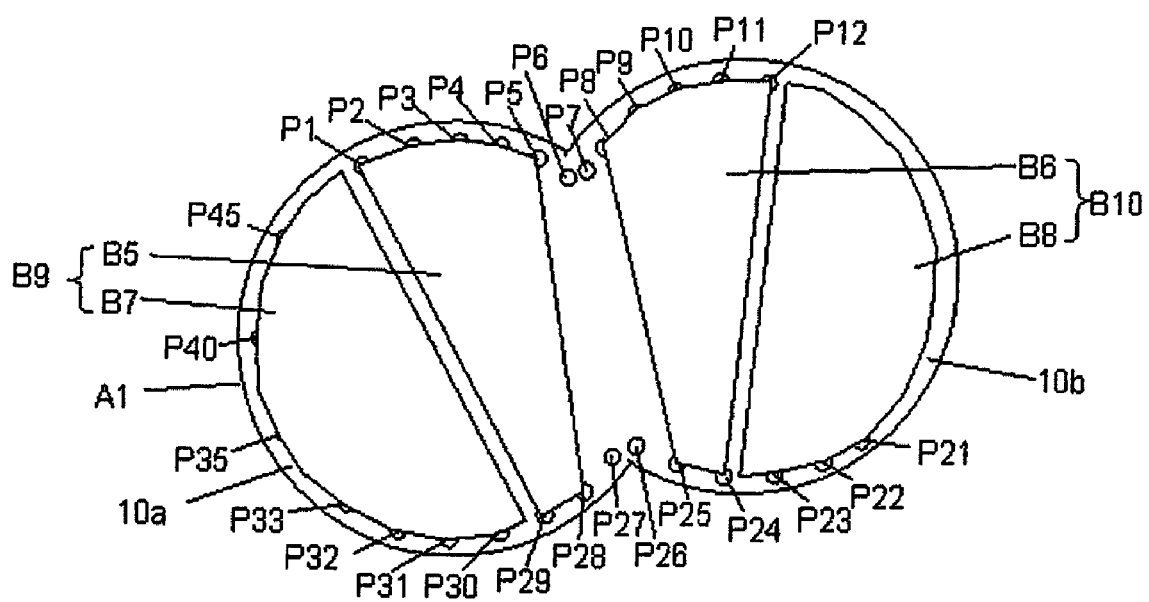
FIG. 7 is an explanation view showing a result of the image processing.

The image processing section 5 forms connection segments connecting the individual undistinguished reference points extracted by the above-mentioned processing to the individual undistinguished reference points in the material region of the same granular material and extracts regions surrounded by the connection segments as material regions B7, B8 corresponding to the agents, respectively. Combined regions of the material regions B5, B6 extracted by the processing method in Second embodiment and the newly extracted material regions B7, B8 may be extracted as material regions B9, B10 (refer to FIG. 7). Whereby, compared to Third embodiment, regions closer to the actual regions of the agents 10a, 10b can be extracted as material regions.

Fifth Embodiment

Figure 8:
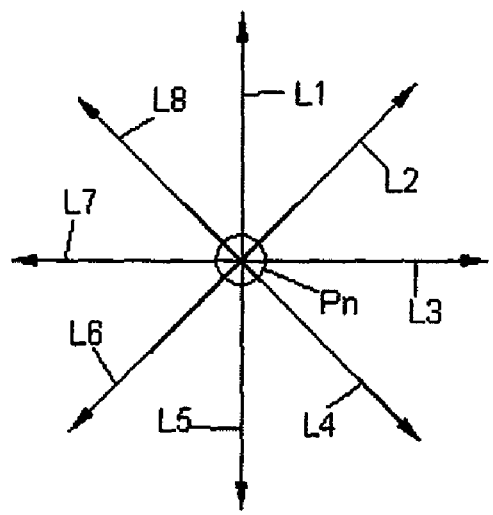
FIGS. 8(a) and 8(b) are explanation views of an image processing method by an inspective device for granular material in accordance with Fifth embodiment of the present invention.
Figure 8:
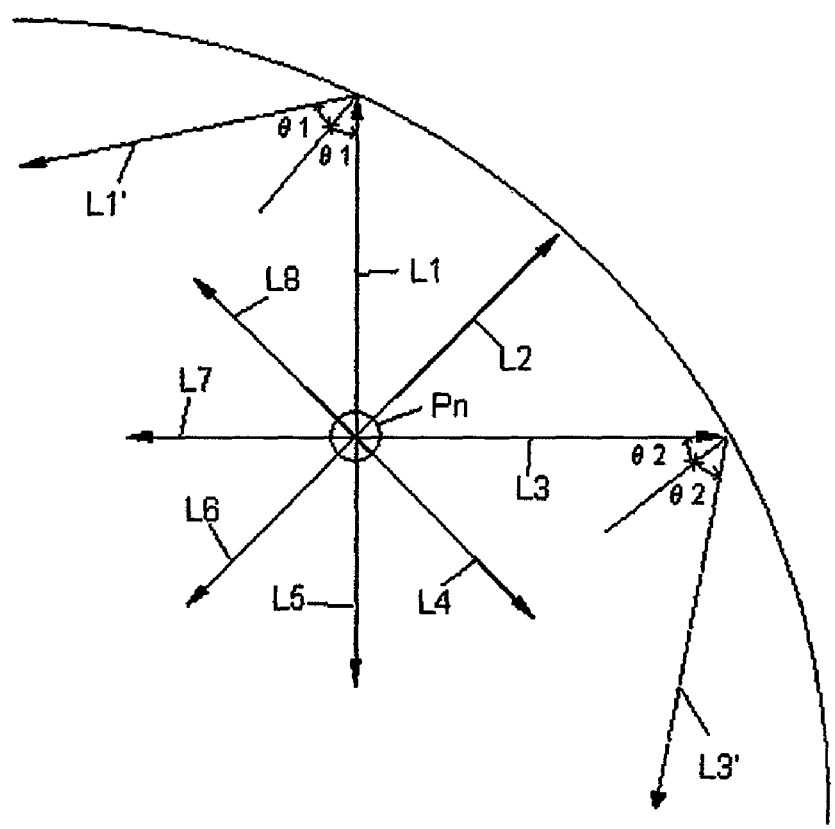

A method of inspecting granular material and an inspective device for conducting the method in accordance with Fifth embodiment of the present invention will be described. In this embodiment, a method of obtaining the material region assigned to the undistinguished reference points is different from the image processing method in Fourth embodiment. According to the image processing method in Fourth embodiment, the material region which can be viewed from the undistinguished reference points extracted by the sixth extraction processing is defined as the material region assigned to the undistinguished reference points. On the contrary, according to the image processing method in this embodiment, as shown in FIG. 8(a), a plurality of search lines radially extending from an undistinguished reference point Pn (for example, L1, L2 . . . L8) are formed at substantially regular intervals (for example, about 45 degrees). Using the plurality of radially extending search lines, the image processing section 5 determines a region until the plurality of radially extending search lines initially intersect connection segments connecting a base point to the base point assigned reference points of the base point extracted by the fifth extraction processing as a region in a material region corresponding to the initially intersecting connection segment. Thus, the image processing section 5 can extract the connection segments connecting the base point to the base point assigned reference points assigned to the base point as well as the region between the undistinguished reference points and the connection segments as material regions.

The image processing section 5 forms the plurality of search lines radially extending from an undistinguished reference point Pn at substantially regular intervals. However, since some of the plurality of search lines (for example, L1) extend from the reference point Pn on the opposite side of the material region, the lines do not intersect the connection segments. Concerning the search lines (for example, L1, L3) which do not intersect the connection segments, as shown in FIG. 8(b), when the search lines L1, L3 are incident on the outline of the massive region A1, the image processing section 5 may allow the search lines L1, L3 to reflect at output angles which are substantially equal to incidence angles θ1, θ3 and determine regions until the reflected L1', L3' initially intersect the connection segment as the material regions assigned to the connection segment. By extracting the material region with more search lines, the region which is closer to shape of the actual granular materials can be extracted. According to this processing method, the region from the undistinguished reference point Pn to the outline LO can be extracted as the material region and thus, the region which is closer to actual region of the actual granular material can be extracted.

Sixth Embodiment

A method of inspecting granular material and an inspective device for conducting the method in accordance with Sixth embodiment of the present invention will be described. According to the image processing methods in Second to Fifth embodiments, compared to the image processing method in First embodiment, the regions closer to the actual regions of the agents 10a, 10b can be extracted as the material regions B5, B6 and so on. However, it is difficult to determine which of the material regions B5, B6 the overlapped portion of the agents 10a, 10b, for example, an intermediate region of the material regions B5, B6 (C3 in FIG. 9) is assigned to. In this embodiment, first, the image processing section 5 forms an odd number of search lines radially extending from the individual reference points in the intermediate region C3. Then, the image processing section 5 obtains the connection segment initially intersecting the formed individual search lines, allocates an identification number of the material region assigned to the connection segment to the respective search line and stores the identification number in the image storage section 4. Then, the processing of allocating the identification number to all search lines is performed. The image processing section 5 examines the identification numbers allocated to the odd number of search lines starting from each reference point and determines that the material region having the largest number of identification numbers as the material region assigned to the reference point.

Figure 9:
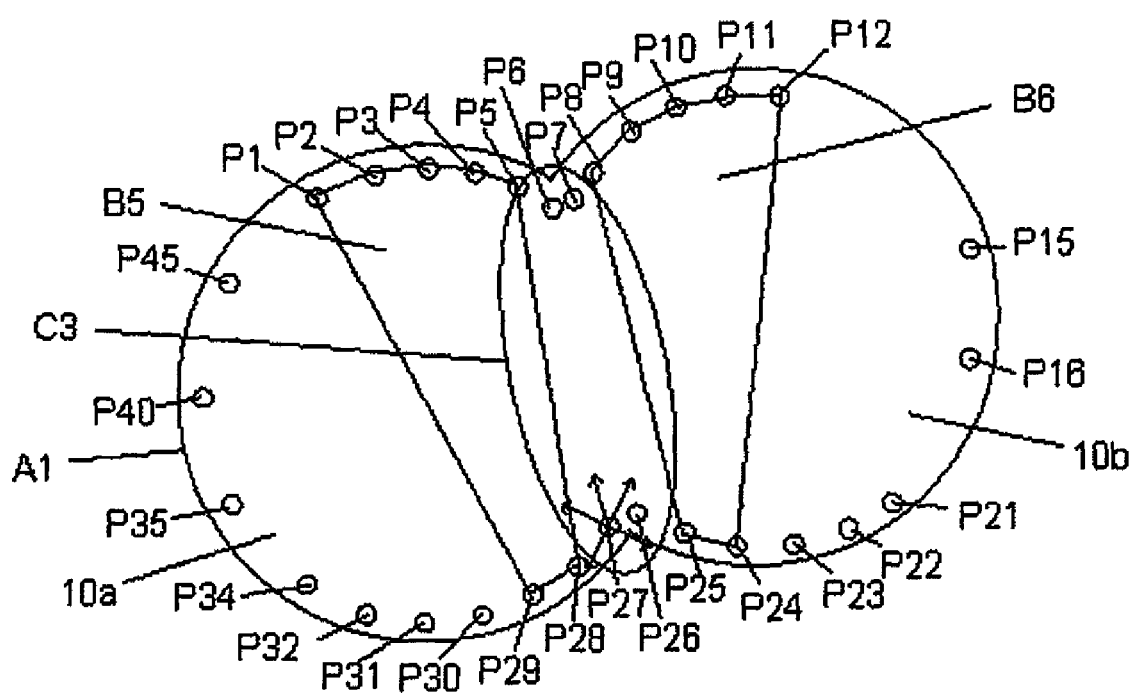
FIG. 9 is an explanation view of an image processing method by an inspective device for granular material in accordance with Sixth embodiment of the present invention.

For example, five search lines radially extending from the reference point P27 in the intermediate region C3 shown in FIG. 9 are formed. When the identification numbers of the material regions B5, B6 are allocated to the search lines, the number of the search lines to which the identification number of the material region B5 is allocated is larger than the number of the search lines to which the identification number of the material region B6 is allocated. In this case, the image processing section 5 determines that the reference point P27 is assigned to the material region B5. The image processing section 5 applies the above-mentioned determination processing to the individual reference points in the intermediate region C3. Then, the image processing section 5 forms connection segments connecting two points among the reference points and the base point in the material region B5 or B6 and reextracts a region surrounded by the connection segments as a material region corresponding to the granular material. Whereby, even in the intermediate region C3 of the material regions B5, B6, it is possible to determine which of the material regions B5, B6 the reference point is assigned to.

Seventh Embodiment

Figure 13:
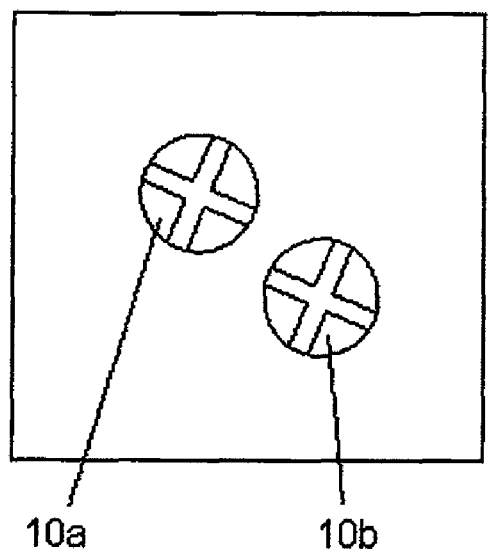
FIGS. 13(a) and 13(b) are views showing images of granular materials to be inspected mounted on the inspection table in the state where the granular materials having a groove on one surface are erected.
Figure 13:
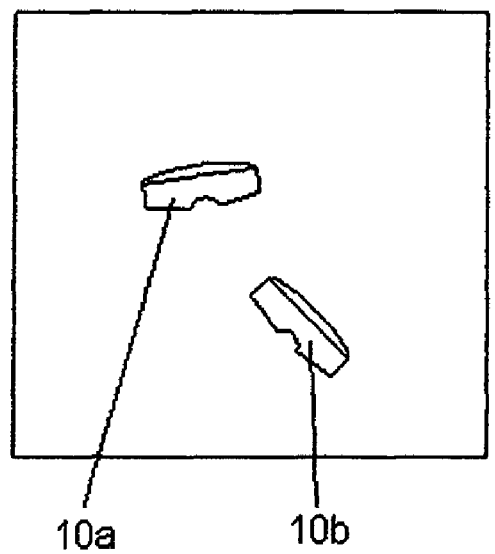

A method of inspecting granular material and an inspective device for conducting the method in accordance with Seventh embodiment of the present invention will be described. In First to Sixth embodiments, even if a plurality of granular materials to be inspected overlap with each other or are in contact with each other, the number of the granular materials can be correctly counted. However, if the agents 10a, 10b having a groove on one surface are erected as shown in FIG. 13(a), when the image processing section 5 performs the image processing described in the above-mentioned embodiments, the outline has a dented portion. For this reason, two base points are extracted. If the number of granular materials is identified based on only the number of base points as in First embodiment, when the agent 10a is erected, it may be wrongly detected that two granular materials exist. In this embodiment, however, even if the agent 10a is erected, the image processing section 5 can correctly determine the number of granular materials.

In this embodiment, as shown in FIG. 10(a), first, the base points P3 and P10 are extracted by repeatedly performing the second to fourth extraction processing described in First embodiment. The following processing is applied to each of the extracted base points P3, P10 from the reference points in the massive region A1 (for example, P1, P2 . . . ). That is, the image processing section 5 performs seventh extraction processing of extracting all reference points which can view only one base point (P3 or P10) through the massive region A1 from the plurality of reference points P in the massive region A1 and extracting reference points located on the opposite side to the base point across the center of the massive region A1 as shape determination points.

For example, for the base point P3, a reference point group consisting of the reference points P1, P2, P4, P5 on the side of the base point P3 (reference point group C4) and a reference point group consisting of the reference points P26, P27, P28 located on the opposite side to the reference point group C4 across the center of the massive region A1 (reference point group C5) are extracted as reference points which can view only the base point P3. The image processing section 5 extracts the reference points P26, P27, P28 belonging to the reference point group C4 as the shape determination points. Similarly, for the base point P10, a reference point group consisting of the reference points P8, P9, P11, P12 on the side of the base point P10 (reference point group C3) and a reference point group consisting of the reference points P23, P24, P25 located on the opposite side to the reference point group C3 across the center of the massive region A1 (reference point group C4) are extracted as reference points which can view only the base point P10. The image processing section 5 extracts the reference points P23, P24, P25 belonging to the reference point group C4 as shape determination points.

After the shape determination points corresponding to each base point are extracted by the seventh extraction processing, a connection segment connecting the shape determination point corresponding to the base point P3 (P26, P27 or P28) to the shape determination point corresponding to the base point P10 (P23, P24 or P25) is formed. Here, given that a pixel value of the background part is 0 and a pixel value of the agents is 1 in the binarized image, since part of a connection segment connecting the base points P3, P10 to each other passes outside of the massive region A1, a pixel value of both ends of the connection segment (base points P3, P10) is 1 and a pixel value of an intermediate portion is 0. Similarly, a connection segment connecting the shape determination points corresponding to the base points P3, P10 to each other (for example, segment S(24-29)) is formed. If the two agents 10a, 10b overlap each other or are in contact with each other, since part of the connection segment S(24-29) passes outside of the massive region A1, a pixel value of both ends of the connection segment is 1 and a pixel value of an intermediate portion is 0. As described above, the image processing section 5 can form the connection segment connecting the shape determination points corresponding two base points to each other and determines that the two base points are assigned to different granular materials if part of the connection segment passes outside of the massive region A1.

Figure 10:
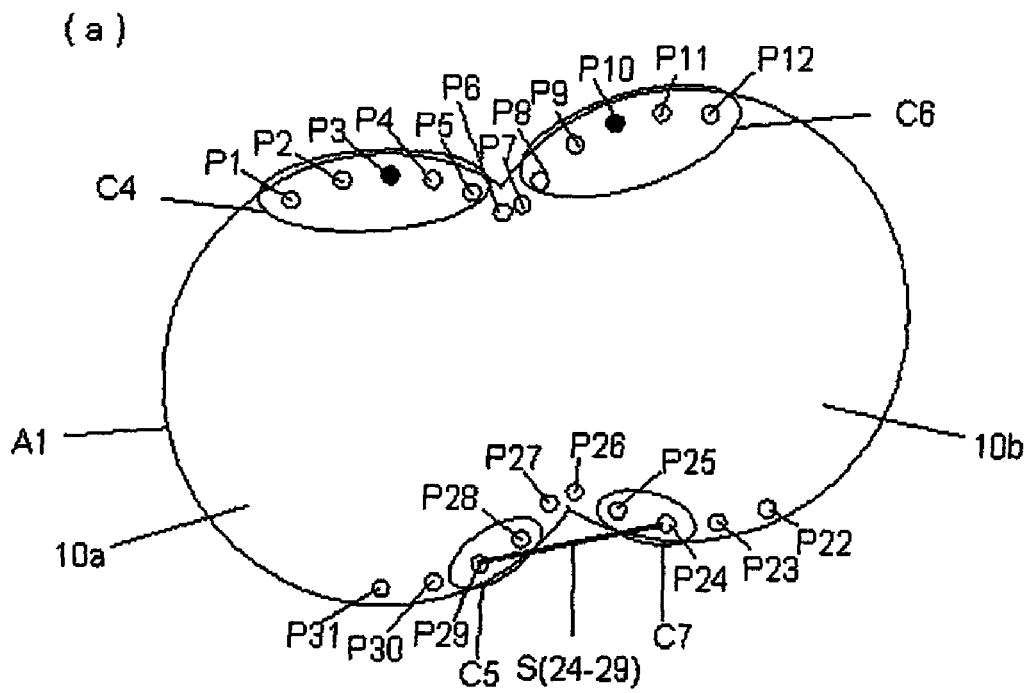
FIG. 10 is an explanation view of an image processing method by an inspective device for granular material in accordance with Seventh embodiment of the present invention.
Figure 10:
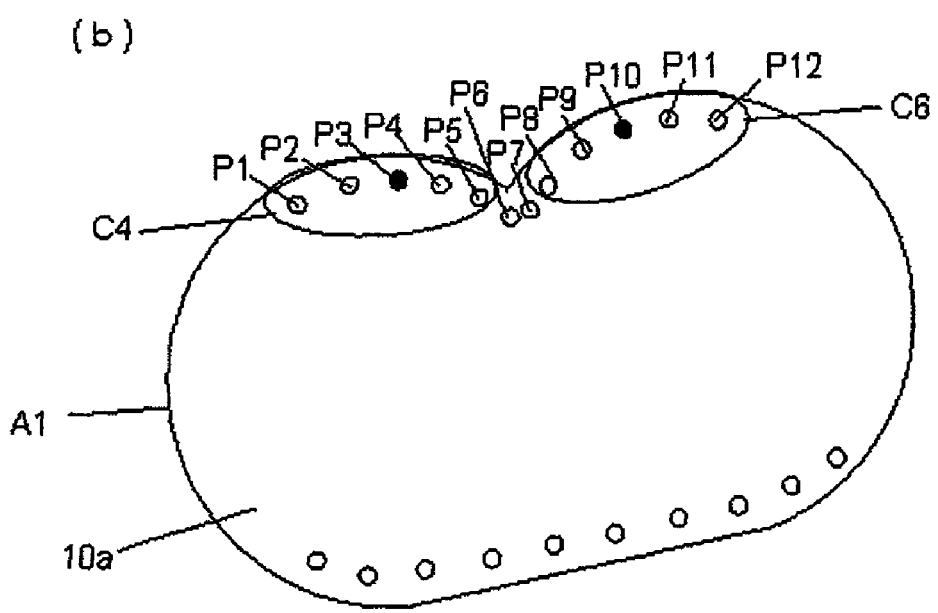

If one agent 10a is erected as shown in FIG. 10 (b), the image processing section 5 can extract two base points P3, P10 by the above-mentioned image processing. However, even if the shape determination points for each of the base points P3, P10 are searched, the reference points located on the opposite side to the base points P3, P10 across the center of the massive region A1 can view both the base points P3, P10, and thus, the shape determination point cannot be extracted. In such case where the determination condition that part of the connection segment connecting the shape determination points to each other passes outside of the massive region A1 does not hold, the image processing section 5 determines that the two base points P3, P10 are assigned to the same granular material. Thus, even if one granular material is erected and two base points are extracted, the image processing section 5 can correctly count the number of granular materials without wrongly detecting existence of two granular materials.

Eighth Embodiment

Figure 11:
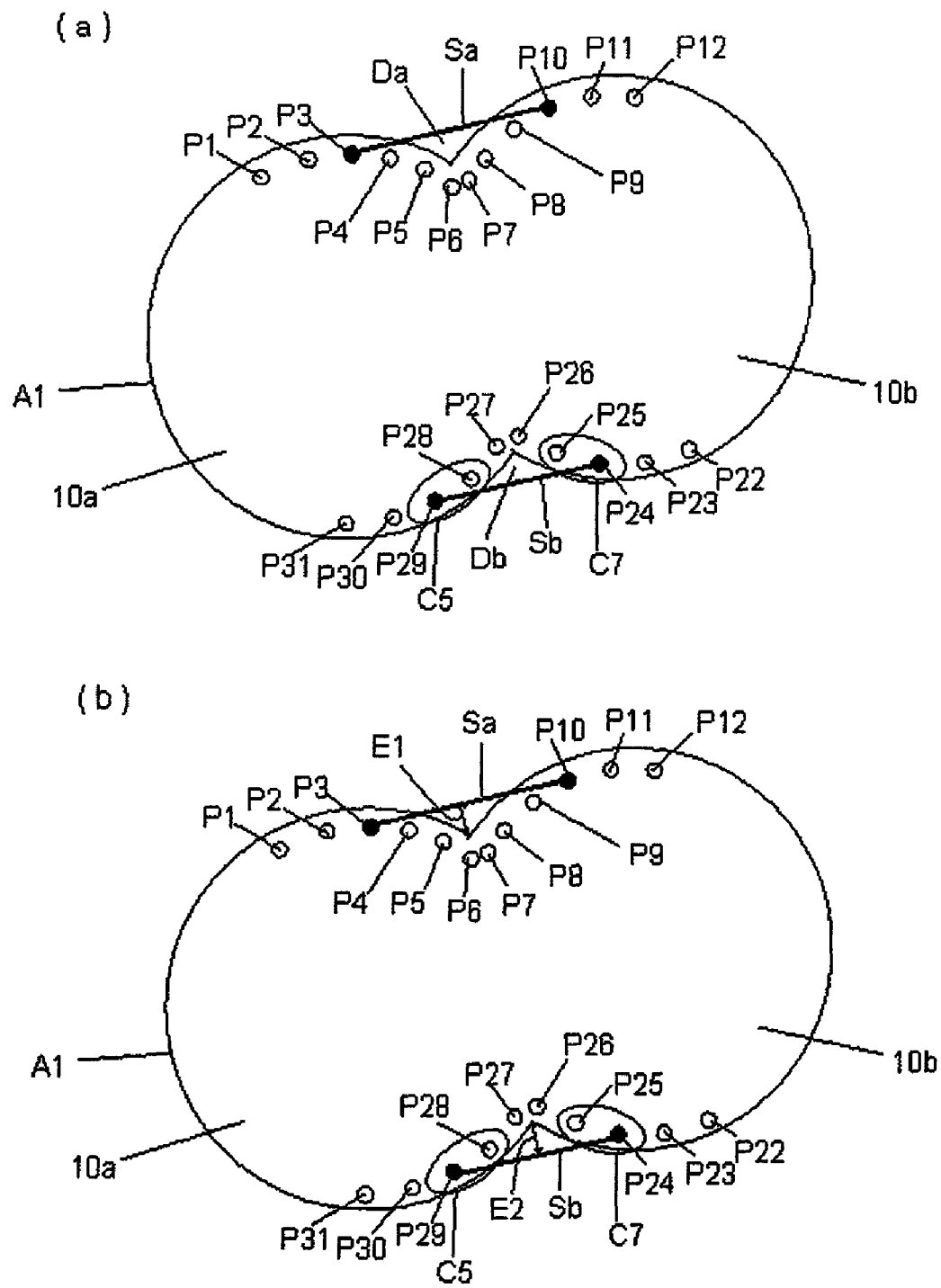
FIG. 11 is an explanation views of an image processing method by an inspective device for granular material in accordance with Eighth embodiment of the present invention.
Figure 12:
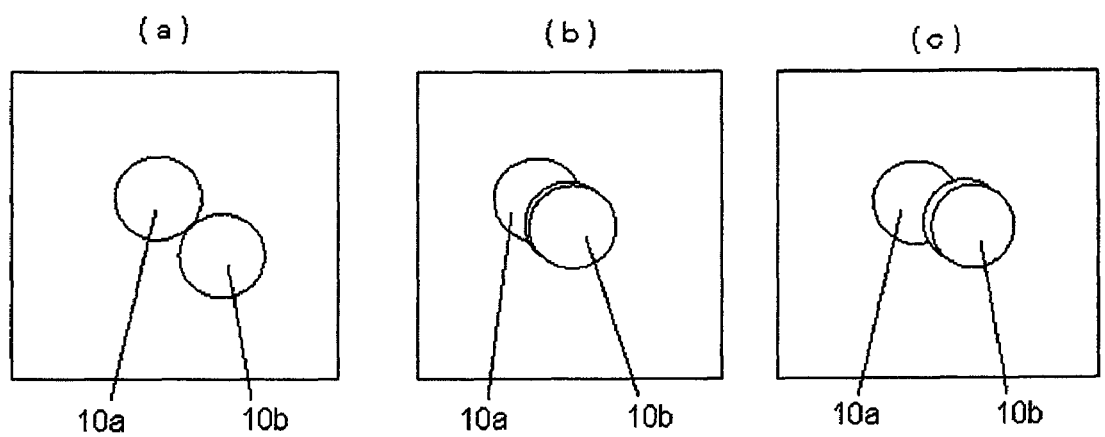
FIGS. 12(a), 12(b) and 12(c) are views showing images of two granular materials to be inspected mounted on an inspection table in the state where the granular materials are in contact with each other or overlap each other.

A method of inspecting granular material and an inspective device for conducting the method in accordance with Eighth embodiment of the present invention will be described. An image processing method in this embodiment is different from the image processing method in Seventh embodiment in the method of determining whether the extracted base points are assigned to different granular materials. In this embodiment, the image processing section 5, as shown in FIG. 11(a), performs eighth extraction processing extracting a region (referred to a first region Da) surrounded by a connection segment connecting the two base points P3, P10 to each other (referred to as a first connection segment Sa) and the outline of the massive region A1 and a region (referred to a second region Db) surrounded by a connection segment connecting the shape determination points P29, P24 corresponding to the two base points P3, P10, respectively, to each other (referred to as a second connection segment Sb) and the outline of the massive region A1. If the two agents 10a, 10b overlap each other as shown in FIG. 11(a), an area of the first region Da is substantially equal to that of the second region Db.

On the other hand, if the agent 10a having a groove on one surface is erected as shown in FIG. 10(b), the first region Da surrounded by the first connection segment Sa and the outline exists, while a region corresponding to the second region Db does not exist. Thus, the image processing section 5 compares the area of the first region Da with the area of the second region Db and determines whether or not the two base points P3, P10 are assigned to different granular materials depending on that the difference between the areas is smaller than a predetermined reference area or not.

In this embodiment, the image processing section 5 takes relatively long time to calculate the areas of the first region Da and the second region Db. Thus, compared to the case of calculating area values, calculation time can be shortened by the following processing. As shown in FIG. 11(b), the image processing section 5 draw a perpendicular from a point on the outline surrounding the first region Da to the first connection segment Sa to obtain a maximum distance between the first connection segment Sa and the point on the outline (referred to as a maximum distance E1) and draw a perpendicular from a point on the outline surrounding the second region Db to the second connection segment Sb to obtain a maximum distance between the second connection segment Sb and the point on the outline (referred to as a maximum distance E2). If the two agents 10a, 10b overlap each other, the maximum distance E1 is substantially equal to the maximum distance E2.

On the other hand, if the agent 10a having a groove on one surface is erected as shown in FIG. 4(b), the first region Da surrounded by the first connection segment Sa and the outline exists, while a region corresponding to the second region Db does not exist. The image processing section 5 can determine whether or not two base points are assigned to different granular materials based on that a difference between the maximum distances E1, E2 is shorter than a predetermined reference distance or not. Even if the granular material is erected and two base points are extracted, the image processing section 5 does not wrongly detect that two granular materials exist. The inspection and judgment section 6 can correctly count the number of the granular materials based on the number of base points assigned to different granular materials.

In this embodiment, a plurality of shape determination points for each of the base points P3, P10 are extracted. Although the above-mentioned determination processing may be applied to all shape determination points, the determination processing is performed multiple times, resulting in an increase in time required for calculation processing. Thus, it is preferred that the image processing section 5 applies the above-mentioned determination processing to only the shape determination points having a maximum distance from the base points P3, P10 among the plurality of shape determination points extracted for the base points P3, P10. Whereby, calculation time necessary for the determination processing can be reduced.

This application is based on Japanese Patent Application No. 2005-048032 and Japanese Patent Application No. 2005-048033 and contents of the patent applications are incorporated into this application by reference.

The invention claimed is:

1. A method of inspecting granular material in a digital image obtained by picking up an image of an imaging region including granular materials to be inspected and digitarizing a pixel value of each pixel of the picked up image, in the case where one massive region is formed of a plurality of material regions corresponding the granular materials which are in contact with each other, for inspecting the granular materials existing in the image region by separating the individual material regions from the massive region comprising:

first extraction processing of extracting the massive region as a target region of image processing from the digital image;

setting processing of dispersely setting a plurality of reference points along the outline of the target region on an inner side of the target region extracted by the first extraction processing;

counting processing of counting the number of other reference points which can be viewed through the target region from individual reference points set by the setting processing;

second extraction processing of extracting a reference point giving a minimum count value obtained by the counting processing as a base point from the plurality of reference points in the target region;

third extraction processing of selecting all reference points which can be viewed through the target region from the base point extracted by the second extraction processing and extracting a region formed by connecting the selected reference points to the base point as the material region of the granular material; and fourth extraction processing of extracting a region in the target region extracting by the third extraction processing except for the material region as a new target region, wherein by repeatedly performing the second to fourth extraction processing, the number of the extracted base points can be counted as the number of granular materials.

2. The method of inspecting granular material as stated in claim 1 further comprising fifth extraction processing of extracting all reference points which can view only one base point of the plurality of base points extracted by repeatedly performing the second to fourth extraction processing through the target region extracted by the first extraction processing as base point assigned reference points for the base point, wherein connection segments connecting the base point extracted by performing the second to fourth extraction processing to all base point assigned reference points assigned to the base point which are extracted by the fifth extraction processing are formed, and a region surrounded by all connection segments thus formed is defined as a material region corresponding to the base point.

3. The method of inspecting granular material as stated in claim 2, wherein the connection segment may be formed by connecting two points of all base point assigned reference points assigned to each base point which are extracted by the fifth extraction processing among the plurality of base points extracted by repeatedly performing the second to fourth extraction processing to each other.

4. The method of inspecting granular material as stated in claim 3 further comprising sixth extraction processing of extracting reference points other than the base point assigned reference points extracted by the fifth extraction processing among all reference points as undistinguished reference points, wherein a material region which can be viewed through the target region extracted by the first extraction processing from the undistinguished reference points extracted by the sixth extraction processing is determined as a material region corresponding to the undistinguished reference points, and the connection segment is formed by connecting two points among the base point corresponding to the material region thus determined, base point assigned reference points and undistinguished reference points to each other.

5. The method of inspecting granular material as stated in claim 3 further comprising sixth extraction processing of extracting reference points other than the base point assigned reference points extracted by the fifth extraction processing among all reference points as undistinguished reference points, wherein a plurality of search lines radially extending from the undistinguished reference points extracted by the sixth extraction processing are formed at substantially regular angles are formed, and a region defined by the individual search lines thus formed and the connection segment connecting two points of all base point assigned reference points assigned to the base point extracted by the fifth extraction processing to each other which intersect the search lines is added to the material region corresponding to the intersecting connection segment.

6. The method of inspecting granular material as stated in claim 2 further comprising sixth extraction processing of extracting reference points other than the base point assigned reference points extracted by the fifth extraction processing among all reference points as undistinguished reference points, wherein a material region which can be viewed through the target region extracted by the first extraction processing from the undistinguished reference points extracted by the sixth extraction processing is determined as a material region corresponding to the undistinguished reference points, and the connection segment is formed by connecting two points among the base point corresponding to the material region thus determined, base point assigned reference points and undistinguished reference points to each other.

7. The method of inspecting granular material as stated in claim 2 further comprising sixth extraction processing of extracting reference points other than the base point assigned reference points extracted by the fifth extraction processing among all reference points as undistinguished reference points, wherein a plurality of search lines radially extending from the undistinguished reference points extracted by the sixth extraction processing are formed at substantially regular angles are formed, and a region defined by the individual search lines thus formed and the connection segment connecting two points of all base point assigned reference points assigned to the base point extracted by the fifth extraction processing to each other which intersect the search lines is added to the material region corresponding to the intersecting connection segment.

8. The method of inspecting granular material as stated in claim 1 further comprising seventh extraction processing of extracting reference points which can view only one base point among a plurality of base points extracted by repeatedly performing the second to fourth extraction processing through the target region extracted by the first extraction processing and are disposed on the opposite side to the base point across the center of the target region, wherein when at least part of connection segments connecting shape determination points corresponding to one base point extracted by the seventh extraction processing to the shape determination points corresponding to other base point passes outside of the target region, it is determined that the plurality of base points are assigned to different granular material, and the number of granular materials is counted based on the number of determined base points assigned to different granular materials.

9. The method of inspecting granular material as stated in claim 1 further comprising seventh extraction processing of extracting reference points which can view only one base point among a plurality of base points extracted by repeatedly performing the second to fourth extraction processing through the target region extracted by the first extraction processing and are disposed on the opposite side to the base point across the center of the target region, and eighth extraction processing of extracting a region surrounded by a first connection segment connecting one base point to the other base point and the outline as a first region and a region surrounded by a second connection segment connecting the shape determination points corresponding to the two base points extracted by the seventh extraction processing to each other and the outline as a second region, a difference between an area of the first region and that of the second region extracted by the eighth extraction processing is smaller than a predetermined reference area, it is determined that the two base points are assigned to different granular material, and the number of granular materials is counted based on the number of determined base points assigned to different granular materials.

10. The method of inspecting granular material as stated in claim 9, wherein a difference between a maximum distance from a point on the outline forming the first region extracted by the eighth extraction processing to the first connection segment and a maximum distance from a point on the outline forming the second region extracted by the eighth extraction processing to the second connection segment is obtained, and when the difference in distance is shorter than a predetermined reference distance, it is determined that the two base point are assigned to different granular materials.

11. The method of inspecting granular material as stated in claim 10, wherein when a plurality of shape determination points are extracted by the seventh extraction processing with respect to the base point extracted by repeatedly performing the second to fourth extraction processing, the shape determination point having the longest distance from the corresponding base point is selected from the plurality of shape determination points, and using the selected shape determination point, the second connection segment is formed.

12. The method of inspecting granular material as stated in claim 9, wherein when a plurality of shape determination points are extracted by the seventh extraction processing with respect to the base point extracted by repeatedly performing the second to fourth extraction processing, the shape determination point having the longest distance from the corresponding base point is selected from the plurality of shape determination points, and using the selected shape determination point, the second connection segment is formed.

13. An inspective device for granular material comprising: an imaging means for picking up an image of an imaging region including granular materials to be inspected; and an image processing section, in the case where one massive region is formed of a plurality of material regions corresponding to the granular materials which are in contact with each other in a digital image obtained by digitarizing a pixel value of each pixel of the image picked up by the imaging means, for separating the individual material regions from the massive region, wherein the image processing section includes a first extraction means for extracting the massive region from the digital image, a setting means for dispersely setting a plurality of reference points along the outline of the target region on the inner side of the target region extracted by the first extraction means, a counting means for counting the number of other reference points which can be viewed through the target region from the individual set reference points, a second extraction means for extracting a reference point giving a minimum count value counted by the counting means as a base point from the plurality of reference points existing in the target region, a third means for selecting all reference points which can be viewed through the target region from the base point extracted by the second extraction means and extracting a region formed by connecting the selected reference points to the base point as a material region of the granular material, a fourth means for extracting a region other than the material region of the target region extracted by the third extraction means as a new target region, and a means for counting the number of granular materials on the basis of the number of base points extracted by repeatedly performing the second to fourth means.

14. An inspective device for granular material comprising: an imaging means for picking up an image of an imaging region including granular materials to be inspected; and an image processing section, in the case where one massive region is formed of a plurality of material regions corresponding to the granular materials which are in contact with each other in a digital image obtained by digitarizing a pixel value of each pixel of the image picked up by the imaging means, for separating the individual material regions from the massive region, wherein the image processing section includes a first extraction means for extracting the massive region from the digital image, a setting means for dispersely setting a plurality of reference points along the outline of the target region on the inner side of the target region extracted by the first extraction means, a counting means for counting the number of other reference points which can be viewed through the target region from the individual set reference points, a second extraction means for extracting a reference point giving a minimum count value counted by the counting means as a base point from the plurality of reference points existing in the target region, a third means for selecting all reference points which can be viewed through the target region from the base point extracted by the second extraction means and extracting a region formed by connecting the selected reference points to the base point as a material region of the granular material, a fourth means for extracting a region other than the material region of the target region extracted by the third extraction means as a new target region, a seventh extraction means for extracting reference points which can view only one base point of a plurality of base points extracted by repeatedly operating the second to fourth extraction means and are located on the opposite side to the base point across the center of the target region as shape determination points, and a means for determining that the plurality of base points are assigned to different granular materials when at least part of connection segments connecting shape determination points corresponding to one base point extracted by the seventh extraction processing to the shape determination points corresponding to other base point passes outside of the target region and counting the number of granular materials on the basis of the number of base points assigned to the determined different granular materials.

15. The inspective device for granular material as stated in claim 14 further comprising an eighth extracting means for extracting a region surrounded by a first connection segment connecting one base point extracted by repeatedly operating the second to fourth extraction means to the other base point and the outline as a first region and a region surrounded by a second connection segment connecting the shape determination points corresponding to the two base points extracted by the seventh extraction processing to each other and the outline as a second region, and a means for determining that the two base points are assigned to different granular materials when a difference between an area of the first region and that of the second region extracted by the eighth extraction processing is smaller than a predetermined reference area and counting the number of granular materials on the basis of the base points assigned to the determined different granular materials.

* * * * *